United States Patent [19]

Shiraishi

[11] Patent Number: 4,848,914

[45] Date of Patent: Jul. 18, 1989

[54] AUTOMATIC BIOCHEMICAL ANALYSIS METHOD AND SYSTEM FOR MEASURING ABSORBANCY

[75] Inventor: Takashi Shiraishi, Ootawara, Japan

[73] Assignee: Kabushiki Kaisha Toshiba, Kawasaki, Japan

[21] Appl. No.: 116,918

[22] Filed: Nov. 5, 1987

[30] Foreign Application Priority Data

Nov. 12, 1986 [JP] Japan .................. 61-267801

[51] Int. Cl.⁴ ........................................... G01N 21/18
[52] U.S. Cl. ..................................... 356/440; 250/576
[58] Field of Search ................. 356/440, 409, 246; 250/576

[56] References Cited

U.S. PATENT DOCUMENTS 2,549,574  4/1951  Condiff ............................ 356/246
4,115,011  9/1978  Brunsting ......................... 356/246
4,329,061  5/1982  Snook et al. ...................... 356/409

Primary Examiner—Vincent P. McGraw
Attorney, Agent, or Firm—Oblon, Spivak, McClelland, Maier & Neustadt, P.C.

[57] ABSTRACT

For higher-speed absorbancy measurement, first and second rotating mirrors are attached individually to the opposite ends of a rotating shaft which is arranged vertically in the center of a reaction-tube table and driven by a motor. A light beam from a prelocated light source, for example, a lamp, is transferred along the axis of the rotating shaft to the first rotating mirror. Reflected by the first mirror, the light beam is applied to a reaction tube, and is reflected by a reflector which is attached to the tube. The light beam reflected by the second rotating mirror on the rotating shaft is transferred along the axis of the shaft to a photodetector, and is detected. In such an arrangement, the respective absorbancies of reaction tubes can be measured in predetermined directions, with respect to the rotating shaft in the center of the reaction-tube table, by simply rotating the shaft.

6 Claims, 3 Drawing Sheets

AUTOMATIC BIOCHEMICAL ANALYSIS METHOD AND SYSTEM FOR MEASURING ABSORBANCY

BACKGROUND OF THE INVENTION

The present invention relates to a method and a system for quickly measuring absorbancy in, for example, an automatic biochemical analyzer.

FIGS. 1 and 2 show a conventional apparatus used in various biochemical analyses of liquid samples, such as serums.

In FIG. 1, a plurality of reaction tubes 1a to 1l are arranged in ring-shaped constant-temperature bath 2, which is located on a rotating table (not shown), thus constituting a reaction line. Tubes 1a to 11, which are made of glass or plastic, and which are optically transparent, rotate at regular cycles in the direction of arrow y of FIG. 1. Although in this description, the reaction tubes are only twelve in number, the number of reaction tubes used in an actual apparatus are several times as many as those illustrated. A washing unit, sample dispensing unit, reagent dispensing unit, mixing unit, etc., (not shown) are arranged in predetermined positions around bath 2, corresponding to the individual reaction tubes. In positions A, B, C and D, the reaction tubes are subjected to specific operations. In the states shown in FIGS. 1 and 2, tubes are at a stop. In position A, as shown in FIG. 1, reaction tubes 1b, 1c and 1d are washed. Thus, samples and reagents, dispensed to and mixed in the reaction tubes before reaching position A, are washed away in position A. Likewise, in position B, another sample is dispensed afresh to the reaction tube 1a washed in position A. A reagent is dispensed to the reaction tube 1l in position C, and a mixture of a sample and the reagent in the reaction tube 1k is performed in position D. A photometric section, which includes the light source, for example, lamp 3 and photodetector 4, is arranged at right angles to the course of rotation of the constant-temperature bath 2 in the direction of arrow y. Thus, optical axis 5 between lamp 3 and photodetector 4 crosses the course of rotation. The quantity of light passing through the tubes varies, due to the states of the liquid mixture. When the reaction tubes intercept optical axis 5, therefore, photodetector 4 obtains absorbancy measurement data in accordance with the degree of transmission.

After the state of FIG. 1 is maintained for a predetermined period of time, ring-shaped constant-temperature bath 2 is rotated in the direction of arrow y for another predetermined period of time. After the individual reaction tubes are moved, the bath 2 is stopped again. This rotation causes each reaction tube to move for a distance equivalent to one revolution plus one pitch.

FIG. 2 shows the arrangement of reaction tubes 1a to 1 in a position reached after such movement of the tubes from the position of FIG. 1. Also in this state, the individual operations are performed in positions A to D.

One cycle is defined as a combination of each rotation time and each stopping time. As such cycles are repeated thereafter, the reaction tubes advance pitch by pitch. Thus, each reaction tube can perform a continuous absorbancy measurement. If twelve cycles of operation are repeated, for example, twelve absorbancy data can be obtained for each reaction tube.

Such an apparatus, however, requires rotation time for absorbancy measurement and stoppage time for the washing, dispensing, and mixing processes. Thus, absorbancy measurement cannot be easily performed at high speed.

Thus, there is a demand for the development of a method for high-speed measurement of absorbancy.

SUMMARY OF THE INVENTION

The object of the present invention is to provide a method and a system for quickly measuring absorbancy in, for example, an automatic biochemical analyzer.

According to an aspect of the present invention, there is provided a method for measuring the absorbancy, which comprises steps of; arranging a plurality of reaction tubes in a ring, locating a rotating shaft in the center of the reaction line at right angles to the reaction line; fixing first and second rotating mirrors individually, at the respective predetermined angles, to the opposite ends of the rotating shaft; rotating the rotating shaft; projecting a light beam towards the reaction tubes on the reaction line by the first rotating mirror; reflecting the light beam reflected from the first rotating mirror toward the second rotating mirror so that the reflected light beam is transmission again through the reaction tubes after transmitting the light beam once through the tubes; and detecting the light beam reflected by the second rotating mirror.

According to another aspect of the invention, there is provided an absorbancy measuring system which comprises; a reaction line with a plurality of reaction tubes arranged in a ring; a rotating shaft located in the center of the reaction line at right angles to the reaction line; first and second rotating mirrors fixed individually, at the respective predetermined angles, to the opposite ends of the rotating shaft; a motor for rotating the rotating shaft; means for projecting a light beam to the reaction tubes on the reaction line by the first rotating mirror; means for reflecting the light beam reflected from the first rotating mirror toward the second rotating mirror so that the reflected light beam is transmitted again through the reaction tubes after transmitting the light beam once transmitted through the tubes, and located on the opposite side of the reaction tubes to the rotating shaft; and means for detecting the light beam reflected by the second rotating mirror.

DETAILED DESCRIPTION OF THE PREFERRED EMBODIMENT

An embodiment of the present invention will now be described with reference to the accompanying drawings.

Figure 3:
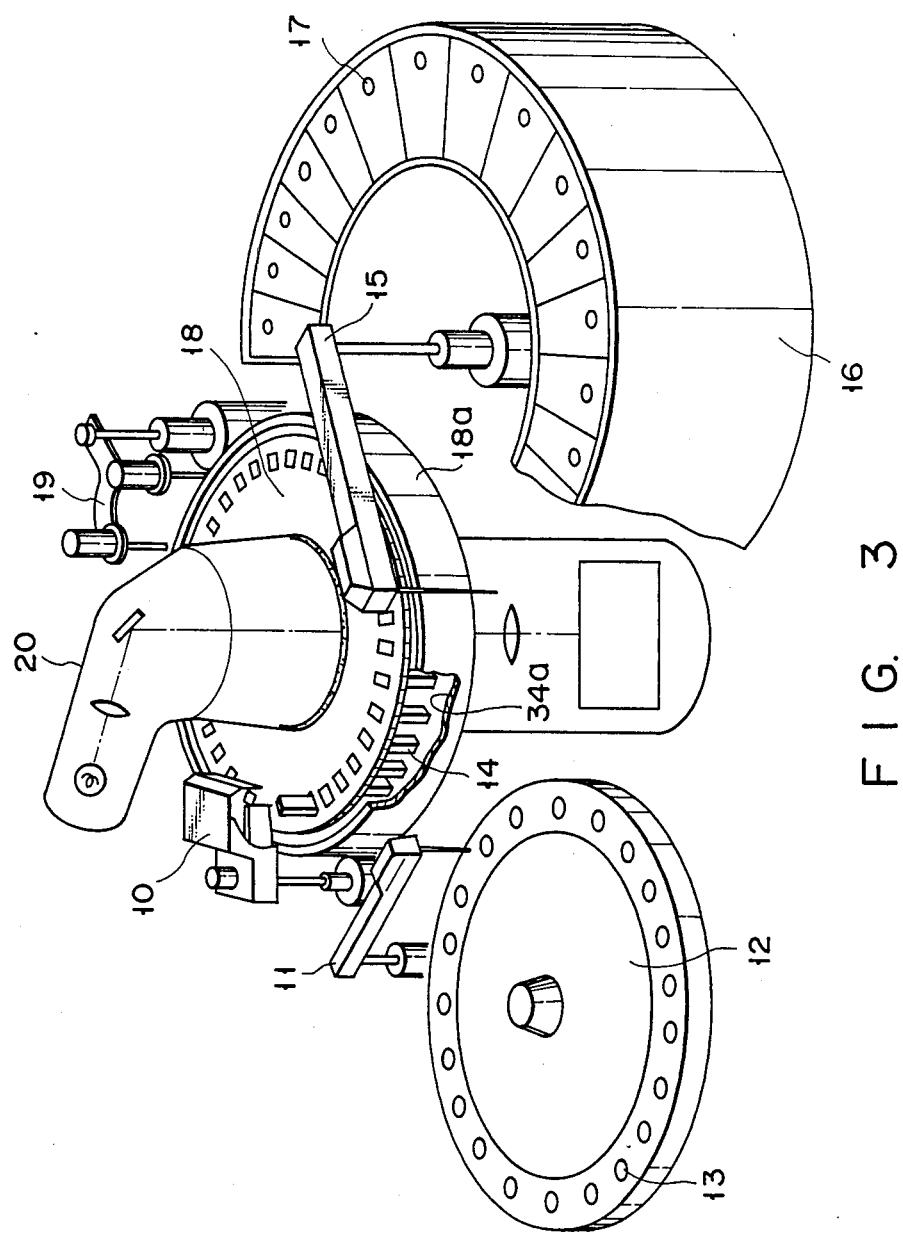
FIG. 3 is a cutaway perspective view showing an outline of an absorbancy measuring system according to an embodiment of the present invention.

Referring to FIG. 3, there is shown a system according to the invention, which comprises washing/drying unit 10 for reaction tubes, sample dispensing unit 11, reagent dispensing unit 15, mixing unit 19, and absorbancy measuring unit 20. Sample dispensing unit 11 is used to dispense samples in sample vessels 13 of sample table 12 to reaction tubes 14 held by reaction-tube table 18. Reagent dispensing unit 15 is used to dispense a reagent in reagent bottles 17 of reagent reservoir 16 to reaction tubes 14. In mixing unit 19, the samples and the reagent in tubes 14 are stirred. Measuring unit 20 measures the respective absorbancies of the sample-reagent mixtures in the reaction tubes.

Figure 4:
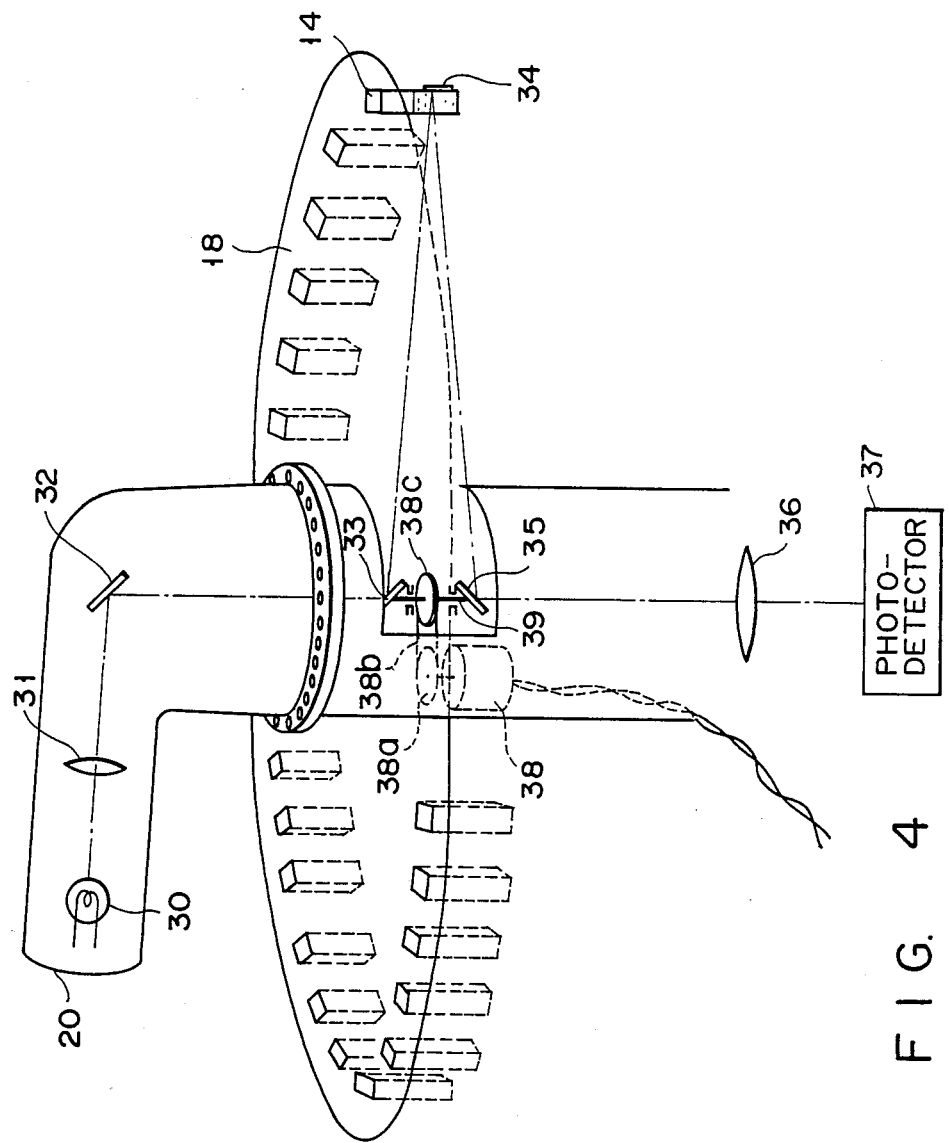
FIG. 4 is an enlarged perspective view showing an arrangement of the principal part of the system of FIG. 3.

In FIG. 4, absorbancy measuring unit 20 includes lamp 30, lenses 31 and 36, stationary mirror 32, rotating mirrors 33 and 35, and photodetector 37. As seen from FIG. 4, a plurality of reaction tubes 14 are arranged in a ring, thus forming a circular reaction line. Reflector 34 for reflecting light beams is attached to part of a lateral face of each reaction tube 14. Reflector 34 serves to reflect those components of a light beam transmitted through each corresponding sample toward the center of the reaction line. Reflector 34 can be easily formed by metal evaporation, for example. Alternatively, reflector 34a may be formed over the inner surface of the peripheral wall of circular reaction chamber 18a (see FIG. 3) which surrounds the reaction line.

Rotating mirrors 33 and 35 are fixed individually, at their respective predetermined angles, to the two opposite ends of rotating shaft 39, which is located in the center of reaction-tube table 18. Shaft 39 is supported in the center of the reaction line, at equal distances from reflectors 34 on individual reaction tubes 14. Rotating shaft 39 is rotated by a rotatory drive unit, i.e., motor 38, through pulley 38a, pulley belt 38b, and pulley 38c. Stationary mirror 32 is located on the upper section of the extension line of rotating shaft 39. The optical axis of a light beam directed from mirror 32 to mirror 33 and that of a beam directed from mirror 35 to photodetector 37 are in alignment with the axis of shaft 39.

The operation of the system with the aforementioned construction will now be described.

A light beam emitted from lamp 30 is converged by lens 31, reflected by stationary mirror 32, and then projected on rotating mirror 33 fixed on rotating shaft 39. After being reflected by mirror 33, the beam is projected to one of reaction tubes 14 on the reaction line, and those components of the beam transmitted through the sample reacted with the reagent, in tube 14, are reflected by reflector 34. The reflected light is transmitted again through the same sample, reflected by mirror 35, and then projected on photodetector 37 through lens 36. The result of detection by photodetector 37 is used for an analysis of the absorbancy of the sample.

When rotating mirrors 33 and 35 are rotated around rotating shaft 39 using motor 38, the light beam from lamp 30 changes its reflecting direction, so that the reaction tube 14, handled as an object of measurement, is replaced with a new one. Thus, the light-beam scanning can be achieved by the rotation of mirrors 33 and 35, so that the respective absorbancies of the samples in the plurality of reaction tubes 14 can be measured with the reaction-tube table 18. Accordingly, the absorbancy measurement can be performed even during the stopping time for the washing, dispensing, or mixing process. In consequence, the measurement can be accomplished while table 18 is rotating, as well as while table 18 is at a stop.

According to the present invention, as described above, the absorbancy measurement can be executed even during the stopping period of reaction-tube table 18, and therefore at a high speed.

Figure 1:
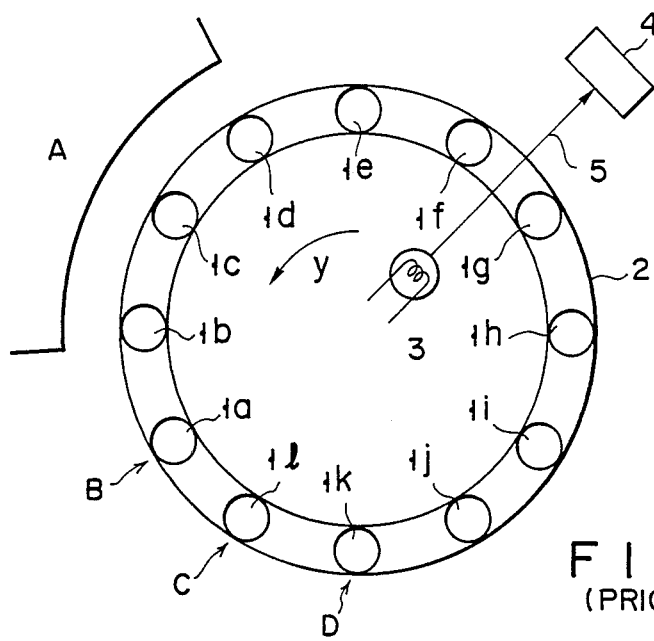
FIGS. 1 and 2 are plan views of a prior art absorbancy measuring apparatus.
Figure 2:
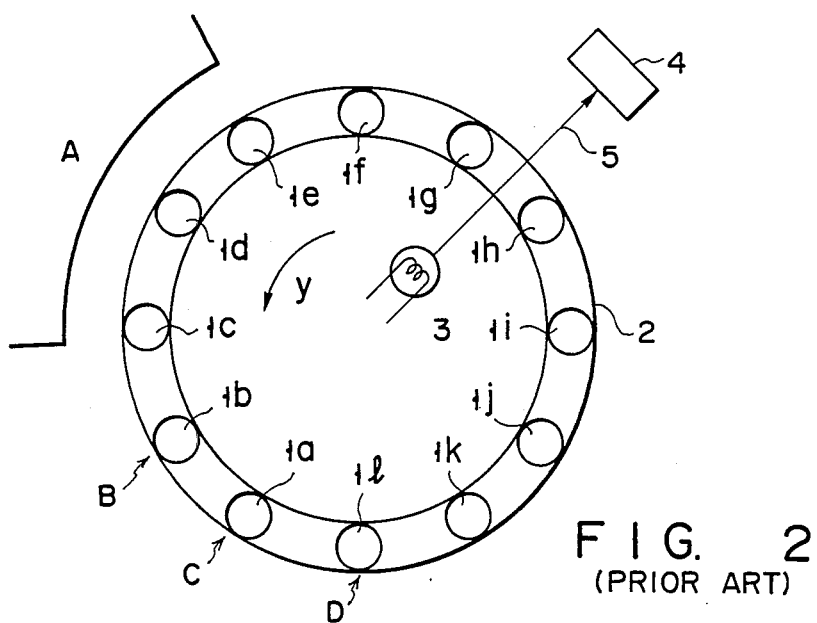

In the conventional apparatus shown in FIGS. 1 and 2, the absorbancy measurement can be achieved by rotating lamp 3 and photodetector 4, while the reaction tubes are at a stop. If the weight of the whole measuring section is taken into consideration, however, this apparatus cannot practically perform high-speed rotation. In this case, a continuous 360° rotation is not executed, due to interference by electric cables for the power supply to lamp 3 and photodetector 4. Such a conventional apparatus cannot ensure high-speed measurement of absorbancy.

In the system according to the present embodiment, on the other hand, only rotating mirrors 33 and 35 are rotated, and lamp 30, lenses 31 and 36, and photodetector 37 are fixed. Also, the high speed rotation can be easily performed, and a continuous 360° rotation can be executed, since there is no problem related to dealing with electric cables.

In the conventional apparatus shown in FIGS. 1 and 2, moreover, the light beam is transmitted only once through each sample. According to this embodiment, however, the beam is transmitted twice through each sample. Therefore, the necessary optical path length in each sample for a certain absorbancy, in the system of this embodiment, can be half the optical path length in the conventional apparatus, so that the sample in each reaction tube can be very small in quantity. In measuring the absorbancy of a certain amount of sample, moreover, the system of the invention can obtain a higher sensitivity than the conventional apparatus, since the optical path length through each sample of the former is twice that of the latter.

It is to be understood that the present invention is not limited to the embodiment described above, and that various changes and modifications may be effected therein by one skilled in the art without departing from the scope or spirit of the invention.

What is claimed is:

1. A method for measuring absorbancy of samples of utilizing a light beam passed through the samples both ways, the method comprising the steps of:

arranging the samples on a reaction line formed in a ring within a reaction chamber;

locating a reflective surface outside of said reaction line on an inner surface of a wall of said reaction chamber facing said reaction line;

radiating the light beam through the samples on the reaction line to the reflecting surface for reflection off the reflective surface back through the samples; and detecting the reflected light beam passed back through the samples by the reflective surface located outside of the reaction line, after the light beam radiated to the samples passes through the samples on the reaction line.

2. A method according to claim 1, wherein the step of locating the reflective surface includes the step of facing the reflective surface to a center of the reaction line.

3. A system for measuring absorbancy of samples by utilizing a light beam passed through the samples both ways, the system comprising:

storing means for storing the samples on a reaction line formed in a ring within a reaction chamber;

scanning means for radiating the light beam through the samples stored in the storing means;

reflecting means having a reflective surface located outside of said reactive line, for reflecting the light beam off the reflective surface back through the samples after the light beam radiated by the scanning means passes through the samples, said reflective surface located on an inner surface of said reaction chamber facing said reaction line; and detecting means for detecting the light beam after the light beam reflected by the reflecting means passes back through the samples.

4. A system according to claim 3, wherein the reflective surface is located to face a center of the reaction line.

5. A system according to claim 3, wherein the scanning means includes:

generating means for generating the light beam;

first mirror means for reflecting the light beam generated in the generating means, thereby radiating the light beam to the samples; and second mirror means for reflecting the light beam reflected by the reflecting means after the light beam reflected by the first mirror means passes through the samples, thereby radiating the light beam to the detecting means.

6. A system according to claim 3, wherein the scanning means is rotated.

* * * * *